United States Patent [19]

Barger et al.

[11] Patent Number: 5,004,853

[45] Date of Patent: * Apr. 2, 1991

[54] CONTINUOUS PROCESS FOR THE PRODUCTION OF 2,6-DIMETHYLNAPHTHALENE

[75] Inventors: Paul T. Barger, Arlington Heights; Timothy J. Barder, Addison; David Y. Lin, Hinsdale; Simon H. Hobbs, Chicago, all of Ill.

[73] Assignee: UOP, Des Plaines, Ill.

[ * ] Notice: The portion of the term of this patent subsequent to May 30, 2006 has been disclaimed.

[21] Appl. No.: 328,654

[22] Filed: Mar. 27, 1989

Related U.S. Application Data

[63] Continuation-in-part of Ser. No. 174,561, Mar. 29, 1988, Pat. No. 4,835,334.

[51] Int. Cl.$^5$ .............................................. C07C 5/22
[52] U.S. Cl. .................... 585/481; 585/482; 585/802; 585/804; 585/807; 585/831; 208/310 Z
[58] Field of Search ............... 585/831, 482, 481, 802, 585/804, 807; 208/310 Z

[56] References Cited

U.S. PATENT DOCUMENTS

| | | | |
|---|---|---|---|
| 3,636,180 | 1/1972 | Broughton | 260/668 A |
| 3,700,744 | 10/1972 | Berger et al. | 585/831 |
| 3,707,550 | 12/1972 | Stine | 260/674 A |
| 3,772,399 | 11/1973 | Hedge | 260/674 SA |
| 3,775,496 | 11/1973 | Thompson | 260/668 F |
| 3,775,498 | 11/1973 | Thompson | 260/668 F |
| 3,780,119 | 12/1973 | Shimada | 260/668 A |
| 3,806,552 | 4/1923 | Oka | 260/668 A |
| 3,888,938 | 6/1975 | Ogasawara | 260/668 A |
| 3,890,403 | 7/1975 | Shimada | 260/674 N |
| 3,895,080 | 7/1975 | Davis | 260/674 A |
| 4,041,089 | 8/1977 | Allen | 260/668 F |
| 4,665,272 | 5/1987 | Bakas | 585/739 |
| 4,735,929 | 4/1988 | Bakas et al. | 502/66 |
| 4,777,312 | 10/1988 | Bakas et al. | 585/482 |
| 4,835,334 | 5/1989 | Hobbs et al. | 585/831 |

FOREIGN PATENT DOCUMENTS 2240632  4/1986  Japan .................. 585/831

*Primary Examiner*—Curtis R. Davis
*Assistant Examiner*—Nhat Phan
*Attorney, Agent, or Firm*—Thomas K. McBride; John F. Spears, Jr.

[57] ABSTRACT

A continuous process is presented for the production and recovery of a high purity stream of 2,6-dimethylnaphthalene. The process comprises the general steps of: fractionating a hydrocarbon feed stream to recover a process stream rich in the various isomers of dimethylnaphthalene; subjecting the process stream rich in isomers of dimethylnaphthalene to a selective adsorption step to produce at least two streams of dimethylnaphthalene isomers, one lean in the 2,6-dimethylnaphthalene isomer and subjecting the stream of dimethylnaphthalene isomers lean in the 2,6 isomer to isomerization to increase the concentration of the 2,6 isomer of dimethylnaphthalene therein and directing the isomerized stream back to the fractionation zone to further processing.

18 Claims, 1 Drawing Sheet

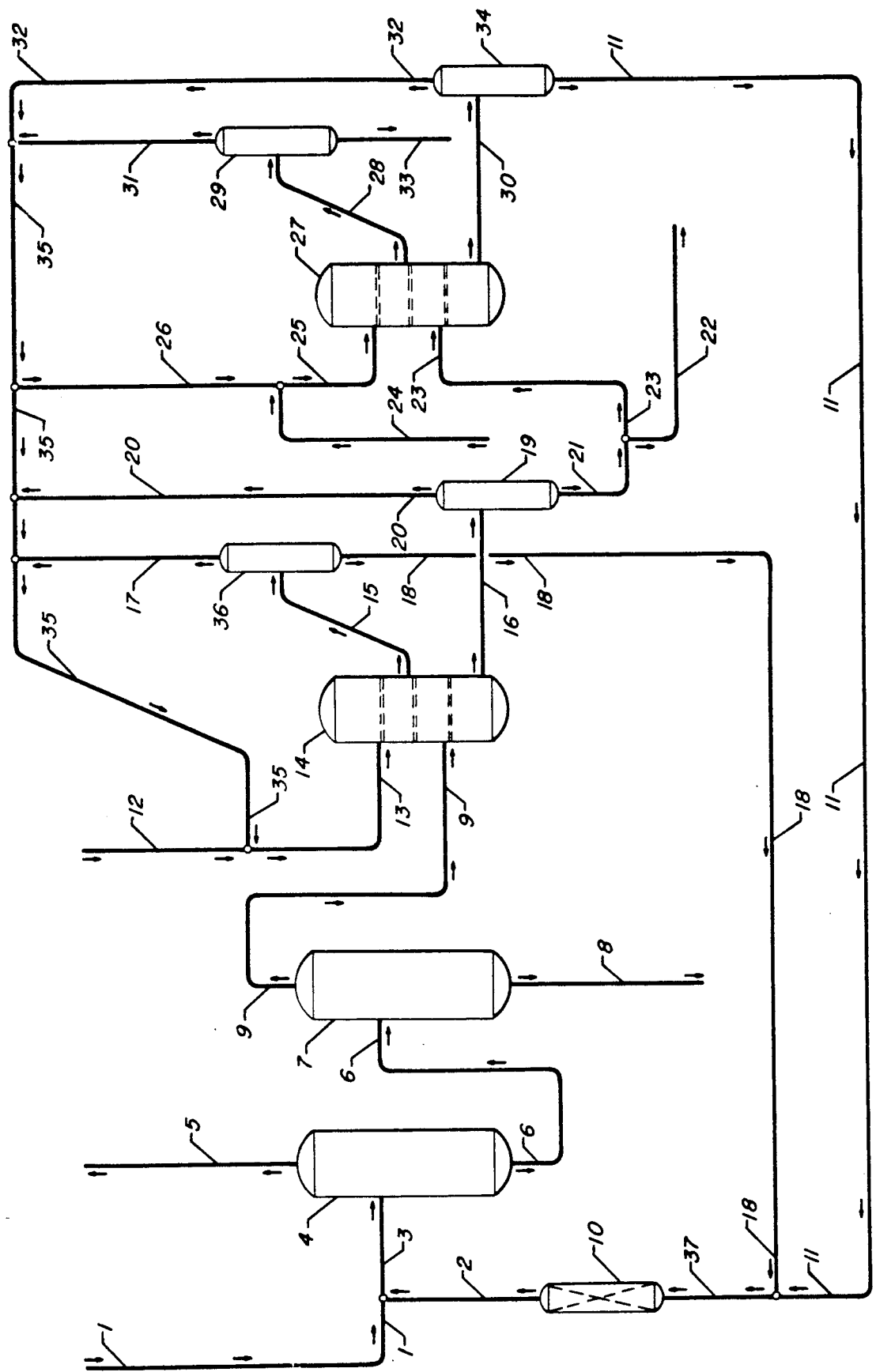

CONTINUOUS PROCESS FOR THE PRODUCTION OF 2,6-DIMETHYLNAPHTHALENE

CROSS-REFERENCE TO RELATED APPLICATION

This application is a continuation-in-part of prior copending application Ser. No. 174,561 filed Mar. 29, 1988, now U.S. Pat. No. 4,835,334.

BACKGROUND OF THE INVENTION

The present invention is related to a process useful in the continuous production of 2,6-dimethylnaphthalene (hereinafter "DMN"). More particularly, this process involves a combination of the process steps of fractionation, adsorptive separation, and isomerization such that other isomers of DMN besides the 2,6 isomer are not able to accumulate in the continuous process.

High purity 2,6-DMN is an important intermediate material in the production of 2,6-naphthalenedicarboxylic acid (2,6-NDCA). Moreover, polymers derived from 2,6-NDCA are known to possess properties that make them more desirable in certain applications compared to other polymers such as those derived from terephthalic acid. Such preferred polymers include polyesters, polyamides, and polyaramides.

It is commerically possible to obtain 2,6-DMN from certain common industrial sources, namely, heavy catalytic reformate, fluid catalytic cracking process recycle oil, or coal tar. Alternatively, it is possible to synthesize an isomeric mixture of DMN's. Regardless of the source of the 2,6-DMN, such sources invariably contain isomers of dimethylnaphthalene besides 2,6-DMN and other impurities which make the production and purification of 2,6-DMN in a continuous process a difficult matter. Particularly troublesome in a continuous process for producing 2,6-DMN is the accumulation of difficult to isomerize isomers of DMN such as 2,7 and 1,7 isomers in the continuous process. Typically, such accumulation would necessitate the use of a drag stream to avoid such detrimental accumulation. The process of this invention is able to produce and purify large quantities of 2,6-DMN without the corresponding production of detrimental amounts of less isomerizable DMN isomers.

INFORMATION DISCLOSURE

The prior art contains references to processes for the production and recovery of aromatic hydrocarbons via a continuous process employing isomerization and adsorptive separation steps. Such processes are disclosed in U.S. Pat. No. 3,700,744 to Berger et al and in U.S. Pat. No. 3,636,180 to Broughton. The U.S. Pat. No. '744 discloses the use of a continuous process to recover ortho-, meta-, and para-xylenes simultaneously and later isomerizing the meta- and para-xylene fraction to produce ortho-xylene in high quantities. The process of this disclosure is distinguished from the instant process in a variety of ways. The adsorptive separation zone of this invention must comprise two adsorptive separation stages whereas that of the U.S. Pat. No. '744 only comprises one adsorptive separation stage. Additionally, the isomerization catalyst is not chosen for its ability to eliminate the accumulation of low reactive aromatic isomers from the continuous process. Finally, and more generally, the entire process of the U.S. Pat. No. '744 is directed at the production of ortho-xylene, and not 2,6-DMN.

The U.S. Pat. No. '180 discloses a process similar to that disclosed in the U.S. Pat. No. '744 patent. However, it is directed towards the production and recovery of a selected aromatic hydrocarbon. The process described in the U.S. Pat. No. '180 does not disclose or claim the use of an adsorbent separation zone utilizing two adsorptive separation stages as does the process of the instant invention. In addition, the U.S. Pat. No. '180 is silent about the use of an isomerization catalyst comprising from 10.0 to 60.0 wt.% of a crystalline aluminosilicate zeolite. Such a catalyst is important in the instant process to isomerize difficult-to-isomerize DMN isomers so as to eliminate the need for a drag stream to remove accumulated isomers.

Current methods of obtaining high purity 2,6-DMN from a hydrocarbon stream containing 2,6-DMN isomers involve the use of sequential unit operations such as adsorptive separation followed by crystallization and/or complexing reactions to achieve a high purity 2,6-DMN product. For example, Hedge teaches in U.S. Pat. No. 3,668,267 that an adsorptive separation process using a sodium-exchanged, Y-type zeolite adsorbent in conjunction with a subsequent crystallization step can be used to obtain acceptably pure 2,6-DMN. In such case, the adsorption step selectively rejected 2,6-DMN to a raffinate stream which stream was, in turn, used as the feed to the crystallization stage. Hedge also disclosed the capability of an L-type zeolite to selectively adsorb the 2,6-DMN isomer from a DMN feed mixture. However, the aforesaid two-stage process (i.e., adsorptive separation followed by crystallization) was disclosed to produce a 2,6-DMN product of superior quality. Subsequently, Hedge in U.S. Pat. No. 3,772,399 teaches a method of separating 2,6-DMN from a mixture containing 2,6-DMN and 1,5-DMN, using a partially dehydrated L-type zeolite adsorbent.

Japanese Disclosure No. 240632/87 is believed to be pertinent to the extent that therein is taught the tendency of 2,6-DMN to be more strongly adsorbed onto a potassium-exchanged type-X zeolite adsorbent relative to the 1,4-DMN isomer. To the contrary, we have discovered that such an adsorbent, when used with either a toluene or monochlorobenzene desorbent material, always exhibits a tendency to reject the 2,6-DMN isomer relative to other DMN isomers.

Other pertinent prior art relating to DMN separation includes U.S. Pat. No. 3,895,080 to Davis which discloses the use of a copper exchanged X-zeolite to selectively retain 2,6-DMN. Also, U.S. Pat. No. 3,707,550 to Stine et al is indicative of an adsorptive separation process.

Processes which employ isomerization steps to produce 2,6-DMN are known in the prior art. One in particular, U.S. Pat. No. 3,890,403 to Shimada et al, describes a combination process that employs an isomerization step to produce 2,6-DMN. The isomerization step disclosed may employ a mordenite catalyst. However, the isomerization catalyst disclosed in the U.S. Pat. No. '403 does not contain a Group VIII metal component. Additionally, this process utilizes steps of partial hydrogenation and dehydrogenation to produce 2,6-DMN. The process of this invention uses only an isomerization reaction zone and adsorptive separation zone to produce high quantities of 2,6-DMN.

Two other U.S. patents that describe processes for producing 2,6-DMN are U.S. Pat. Nos. 3,775,496 and 3,775,498 both to Thompson. However, the processes described in these two patents are directed towards converting a specific hydrocarbon such as 5-m-tolylpentene-2 or 5-o-tolylpentene-2 to 2,6-DMN using steps of cyclization, dehydrogenation, and isomerization.

Isomerization processes employing a catalyst comprising a platinum group metal component and a crystalline aluminosilicate zeolite as processes for the isomerization of hydrocarbons is disclosed in U.S. Pat. No. 4,665,272 to Bakas et al. The U.S. Pat. No. '272 discusses the isomerization of a light hydrocarbon in the presence of a catalyst comprising a Group VIII metal component and the crystalline aluminosilicate zeolite known as mordenite. In the U.S. Pat. No. '272 disclosure, the formed catalyst is acid treated such that it results in a catalyst comprising a surface area of greater than 580 m$^2$/g. The catalyst disclosed in the '272 patent is merely exemplary of catalysts that might be useful in the isomerization step of the instant process. Finally, isomerization processes and catalysts utilizing mordenite as a primary component of the catalyst are disclosed in U.S. Pat. Nos. 4,041,089, 3,806,552, 3,888,938, and 3,780,119. While all of these references disclose isomerization catalysts comprising mordenite, none disclose the usefulness of from 5 to 60 wt. % mordenite in conjunction with a platinum group metal component in an isomerization catalyst which is useful in isomerizing all types of isomers of DMN into the useful isomer 2,6-DMN.

BRIEF SUMMARY OF THE INVENTION

This invention provides an efficient and continuous process for the production and recovery of 2,6-DMN from a feedstock comprising a mixture of DMN isomers. The continuous process is especially unusual in that it is able to produce a continuous product stream of 2,6-DMN at high recovery rates without the need for a drag stream to prevent the accumulation of low reactivity DMN isomers.

A broad embodiment of this invention is a continuous process for the production of 2,6-DMN including a two-stage adsorptive separation step for obtaining a purified stream of 2,6-DMN. The purified 2,6-DMN product stream is produced by a multi-step process wherein the first step comprises separating in a fractionation step a feedstream comprising DMN isomers, and hydrocarbons with boiling points greater than and less than the DMN isomers, to produce a first process stream comprising essentially DMN isomers. The first process stream comprising essentially DMN isomers is then passed into an adsorptive separation step comprising a first stage which employs a first stage adsorbent comprising a potassium-exchanged X-zeolite and a first stage desorbent material. The first stage is operated at 2,6-DMN rejective conditions to produce a first stage extract and raffinate product. At least a portion of the raffinate product of the first stage is then fed to the second stage which employs a second stage adsorbent comprising a carbonaceous material or potassium-exchanged X-zeolite and a second stage desorbent material. The second stage is operated at 2,6-DMN adsorptive conditions, thereby producing a second stage extract product containing purified 2,6-DMN. The second stage extract product containing purified 2,6-DMN is recovered from the process. Additionally, the first stage extract product produced in the adsorptive separation step is contacted with an isomerization catalyst comprising a crystalline aluminosilicate zeolite and a platinum group metal component at isomerization reaction conditions in an isomerization reaction zone to produce an isomerization reaction zone product stream. The isomerization reaction zone product stream is characterized in that the concentration of 2,6-DMN in the isomerization reaction zone product stream is greater than the concentration of 2,6-DMN in the first stage extract product. The isomerization reaction zone product stream is finally passed into the fractionation step for further processing. In a preferred embodiment, the process of the instant invention is a continuous process for the production of 2,6-DMN including a two-stage adsorptive separation step. The continuous process begins by passing a fresh feedstream comprising a mixture of DMN isomers including 2,6, 2,7, and 1,7 isomers and an isomerization reaction zone product stream into a fractionation step. In the fractionation step, the fresh feedstream is separated into a heavy hydrocarbon fraction, a light hydrocarbon fraction, and a first process stream fraction comprising DMN isomers including 2,6, 1,7 , and 2,7 isomers of DMN. The first process stream fraction comprising the various isomers of 2,6-DMN above is then passed into a two-stage adsorptive separation step comprising a first stage employing a first stage adsorbent comprising a potassium-exchanged X-zeolite and a first stage desorbent material and operating at 2,6-DMN rejective conditions to produce a first stage extract and raffinate product. At least a portion of the raffinate product of the first stage is fed to the second stage which employs a second stage adsorbent comprising a carbon material and a second stage desorbent material. The second stage is operated at 2,6-DMN adsorptive conditions, thereby producing a second stage extract product containing purified 2,6-DMN. The second stage extract product stream containing purified 2,6-DMN is thereafter recovered. The first stage extract stream is passed into an isomerization reaction zone operating at isomerization reaction conditions including a temperature of from 300° to 450° C., a pressure of from 1 to 20 atmospheres, and a liquid hourly space velocity of from 0.5 to 5 hr$^{-1}$ and into contact with an isomerization catalyst. The isomerization catalyst comprises from 10 to 60 wt. % of a crystalline aluminosilicate and from 0.1 to 5.0 wt. % of a platinum group metal component. An isomerization reaction zone product stream having a 2,6-DMN concentration greater than that of the first stage extract stream entering the isomerization reaction zone is the product of the isomerization reaction step. The isomerization reaction step product is then returned to the fractionation step for further processing.

BRIEF DESCRIPTION OF THE DRAWING

The accompanying drawing is a simplified process flow diagram of a preferred embodiment of the invention.

DESCRIPTION OF THE DRAWING

The accompanying drawing is a simplified process flow diagram of a preferred embodiment of the invention. Referring to the drawing, a hydrocarbon feed stream comprising isomers of DMN is fed through line 1 and combined with the isomerization reaction zone product stream in line 2 comprising DMN isomer products of the isomerization reaction zone 10. The streams are combined in line 3 and fed into a first fractionation means 4 wherein components having lower boiling points than the DMN isomers are substantially removed in line 5 from the DMN isomer comprising hydrocarbon mixture. The heavy hydrocarbon mixture comprising DMN isomers is removed from the first fractionation means 4 in line 6 and passed into a second fractionation means 7 where hydrocarbons having a boiling point higher than the DMN isomers are removed from the hydrocarbon mixture and removed from the process in line 8. The hydrocarbon mixture comprising DMN isomers in them is withdrawn in line 9 from the second fractionation means 7 and passed into the first stage adsorptive separation means 14 of the adsorptive separation section.

In the first stage adsorptive separation means 14, make-up desorbent in line 12 and recycle desorbent from line 36 is combined in line 13 before entering the first stage adsorptive separation means 14. The desorbent in line 13 and DMN isomer containing hydrocarbon mixture in line 35 are fed into the first stage adsorptive separation means 14 from which is produced a first stage extract stream 15 and a first stage raffinate stream 16. The first stage extract stream 15 is passed into a desorbent recovery means 36 from which a recycle desorbent stream 17 is produced, along with a first stage extract product stream 18. The first stage raffinate stream 16 is directed into desorbent recovery means 19 from which recycle desorbent stream 20, and first stage raffinate product stream 21 comprising 2,6-DMN and other DMN isomers is produced. The first stage raffinate product stream 21 may be partially or totally withdrawn from the process in line 22, or partially or totally directed to the second stage adsorptive separation means 27 through line 23.

The second stage adsorptive separation means 27 accepts a feed stream of desorbent in line 25 and the first stage raffinate product stream comprising DMN isomers in line 23. The desorbent in line 25 may be made up of fresh desorbent from line 24, or recycle desorbent from line 26 or a mixture of both. The second stage adsorptive separation means 27 produces a second stage extract stream 28 and a second stage raffinate stream 30. The second stage extract stream 28 is directed to a desorbent recovery means 29 from which a desorbent recycle stream 31 is produced, and from which an extract product stream 33, rich in the 2,6 isomer of DMN is produced. The second stage raffinate is directed to desorbent recovery means 34 from which a desorbent recycle stream 32 is produced as well as a second stage raffinate product stream 11 comprising primarily non-DMN hydrocarbons.

The first stage extract product stream 18 is combined with second stage raffinate product stream 11 and is directed as the combined feed stream 37 to the isomerization reaction zone 10 where the DMN isomers are reacted to produce an isomerization reaction zone product stream 2 which comprises a higher concentration of 2,6-DMN isomer than in the isomerization reaction zone combined feed stream 37. The isomerization reaction zone product stream 2 is then recycled and combined with the fresh feed of stream 1 for further processing.

The desorbent recycle streams produced by the various desorbent recovery means 19, 29, 34, and 36 may all be combined in a common line 35 before being supplied to the first or second stage adsorptive separation means.

DETAILED DESCRIPTION OF THE INVENTION

A continuous process has been developed for the production and recovery of 2,6-DMN from a hydrocarbon feedstock comprising various isomers of DMN. The continuous process is capable of enhancing the concentration of 2,6-DMN isomers in a DMN isomer containing hydrocarbon stream, and thereafter recovering a highly purified 2,6-DMN product.

According to the present invention, there is provided a continuous process for the production of 2,6-DMN which comprises the steps of fractionation, adsorptive separation, and isomerization. The feedstock useful in the process of the present invention must comprise DMN isomers. DMN has the structure:

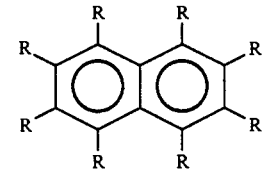

where R is either hydrogen or —CH$_3$ and where only two of the R groups represent —CH$_3$. The preferred DMN isomer of the instant process, 2,6-DMN, has the structure:

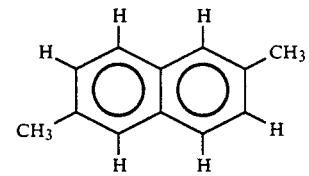

DMN isomers may be found in most hydrocarbon liquid containing heavy aromatic components such as an aromatic alkylate stream. A preferred source of DMN isomers is the heavy hydrocarbon fraction of a catalytic reforming process. Such a heavy fraction would typically contain catalytic reforming product hydrocarbons which boil at a temperature above 200° C., and preferably above 230° C. It is anticipated that any hydrocarbon containing isomers of DMN may be useful as the feedstock to the instant process. In fact, it is conceivable that a feedstock comprising DMN isomers but containing no 2,6 isomers could be utilized in the instant process if first fed to the isomerization step. Therefore, it is preferred that the feedstock utilized comprise at least 50 wt. % DMN isomers and preferably at least 75 wt. % DMN isomers.

In the instant process, a DMN isomer-containing feedstock as described above may either be combined with an isomerization reaction zone product stream as described further below or passed alone into a fractionation step. The purpose of the fractionation step is to remove those hydrocarbons from the feedstock which are not DMN isomers and which boil at temperatures lower and higher than the desired DMN isomer feed components. The fractionation step may be comprised of a single fractionation column with multiple product draw points, or multiple fractionation columns. Additionally, the fractionation columns may be combined with vapor/liquid separators to affect the desired separations. It is preferred however that the fractionation step consist of two fractionation columns, specifically, a stripping column and a rerun column. In the stripping column, hydrocarbons boiling at temperatures lower than the DMN isomers are removed from the admixed hydrocarbon feedstock as a stripper overhead product. The remaining hydrocarbons including the DMN isomers are withdrawn from the stripper as stripper bottoms and passed into the rerun column. In the rerun column, hydrocarbons including the DMN isomers are vaporized and removed from the rerun column as an overhead product while hydrocarbons with boiling points greater than the 2,6-DMN isomers remain in liquid form and are removed from the bottoms of the rerun column and the process as a heavy hydrocarbon by-product.

The hydrocarbon feedstock admixture comprising DMN isomers and essentially free of hydrocarbon components of lower and highber boiling points than the DMN isomers is fed into an adsorptive separation zone in which the 2,6-DMN isomer is separated and recovered as the desired product of the reaction and in which the remaining DMN isomers are recovered and directed to an isomerization reaction zone for further processing. By "essentially free" as referred to hereinabove and generally, it is meant that the stream in question contains less than 5 wt. % and preferably less than 2 wt. % of the deleterious component(s) of which it is to be essentially free.

The adsorptive separation step of the instant continuous process may be performed using a variety of operating techniques. For instance, the adsorbent may be retained as a fixed bed or transported through the adsorption zone as a moving bed. In addition, techniques may be employed to simulate the movement of the adsorbent bed. The adsorptive separation step can therefore comprise a simple swing-bed system with one or more beds of adsorbent being used to collect the desired chemical compound(s) while previously used beds are being regenerated by the use of a desorbent and possibly by a simultaneous temperature increase, pressure decrease, or a combination of two or more of these commonly used regeneration techniques. A further possible variation in the operation of the adsorptive separation zone results from the possibility of operating the adsorbent beds under either vapor phase or liquid phase conditions. The use of liquid phase methods is preferred.

Certain benefits are obtained by using a simulated moving bed of adsorbent. These benefits include the continuous production of a high purity product stream while avoiding attrition of the adsorbent. Preferably, the countercurrent flow of the bed of solid adsorbent and the various entering liquid streams, such as the feed and desorbent streams, is simulated. Two separate actions are involved in this simulation. The first of these is the maintenance of a net fluid flow through the bed of adsorbent in a direction opposite to the direction of simulated movement of the adsorbent. This is performed through the use of a pump operatively connected in a manner to achieve this circulation along the length of the entire bed of adsorbent. The second action involved in simulating the movement of the adsorbent is the periodic actual movement of the location of the various zones, such as the adsorption zone, along the length of the bed of adsorbent. This actual movement of the location of the various zones is performed gradually in a unidirectional pattern by periodically advancing the points at which the entering streams enter the adsorbent bed and the points at which the effluent streams are withdrawn from the adsorbent bed. It is only the locations of the zones as defined by the respective feed and withdrawal points along the bed of adsorbent which are changed. The adsorbent bed itself is fixed and does not move.

The bed of adsorbent may be contained in one or more separate interconnected vessels. At a large number of points along the length of the bed of adsorbent, typically 8–20, the appropriate openings and conduits are provided to allow the addition or withdrawal of liquid. At each of these points, there is preferably provided a constriction of the cross-section of the bed of adsorbent by a liquid distributor-collector. These may be similar to the apparatus described in U.S. Pat. Nos. 3,208,833; 3,214,247; and 3,523,762. These distributor-collectors serve to aid in the establishment and maintenance of plug flow of the fluids along the length of the bed of adsorbent. The two points at which any one stream enters and the corresponding effluent stream leaves the bed of adsorbent are separated from each other by at least two or more potential fluid feed or withdrawal points which are not being used. For instance, the DMN isomer-containing feed stream may enter the adsorption zone at one point and flow past nine potential withdrawal points and through nine distributor-collectors before reaching the point at which it is withdrawn from the adsorbent bed as the raffinate stream.

The gradual and incremental movement of the adsorption zone is achieved by periodically advancing the actual points of liquid addition or withdrawal to the next available potential point. That is, in each advance of the adsorption zone, the boundaries marking the beginning and the end of each zone will move by the relatively uniform distance between two adjacent potential points of liquid addition or withdrawal. The majority of the zone is unaffected and remains intact since the zone extends past several of these fluid transfer points.

The switching of the fluid flows at these many different locations may be achieved by a multiple-valve manifold or by the use of a multiple-port rotary valve. A central digital controller is preferably used to regualte the operation of the rotary valve or manifold.

It is important to note that an adsorptive separation process step, as any process operation "unit", may be serially connected, in stages, to other adsorptive separation process steps to effect a desired overall operational result. Generally, this is not necessary, insofar as an adsorbent and desorbent system employed in the individual unit operation is normally selected so as to be adequate to effect the desired separation in a single stage operation. However, to the extent that such single stage adsorptive separation is not capable of achieving the desired product, two or more such stages may be linked serially to effect such result.

It will be clear to one ordinarily skilled in the art that such staging may be accomplished in the same apparatus if the stages are performed with intermediate product storage in an appropriate time sequence, that is, in a "blocked-out" operating mode. Of course, such blocked-out operation in an adsorptive separation process is only likely to be economically feasible on a commerical basis, given the complexity of adsorbent loading and unloading, if the same adsorbent is used in both stages. Moreover, the similarity or incompatibility of physical and/or chemical properties of the desorbent(s)

required in each stage may determine the feasibility of utilizing a blocked-out, staged operation.

Furthermore, ordinarily, in a staged process, each stage accomplishes the same purpose and in the same manner as the stage(s) which precede it, however, the product of such downstream stage(s) is (are) improved relative to the product of the upstream stage(s) because of the enhanced quality of the material fed to such downstream stage(s) relative to the material fed to the upstream stage(s). Thus, ordinarily, each stage is an operational replicate of each other stage. However, such need not necessarily be the case. Note that it is possible to utilize the same apparatus for two distinct unit operations depending upon the operating technique employed in such stage(s) at the time in question. For example, a distillation column may be used to separate various mixtures depending, among other things, upon the amount of energy input into the reboiler of the column and the flow rates into, within and out of the column. Correspondingly, in one embodiment of our invention, we alter the operation of a single adsorbent-/desorbent apparatus by appropriate adjustment of the external flow rates of the stage. That is, specifically, in one embodiment of our invention, by merely varying one or more of the unit operation's external flow rates, we can selectively direct the desired component (in this case, 2,6-DMN) of the feed stream to either the extract stream (i.e., 2,6-DMN extractive conditions) or raffinate stream (i.e., 2,6-DMN rejective conditions) of such stage, without changing the type of adsorbent or desorbent in such apparatus. Such a purely operating variable change allows for the employment of an efficient blocked-out operation in a single apparatus. Furthermore, we have discovered the appropriate adsorbent-desorbent combination which allows for this operating technique to be employed for purifying 2,6-DMN. Specifically, the use of a carbon adsorbent material or an adsorbent potassium-exchanged X-type zeolite along with a desorbent comprising toluene has been shown to function adequately.

In a preferred embodiment of the process of our invention, we have discovered that an adsorptive separation step comprising two adsorptive separation stages is most effective in affecting the separation of 2,6-DMN in the continuous process of the instant invention. Each stage utilizes an appropriate, but distinct, adsorbent material and preferably a common desorbent material. Although such a dual adsorbent system could be run in a single apparatus, in a blocked-out manner, as aforesaid, it would usually be impractical to intermediately store interstage product(s) and tolerate the requisite process downtime between alternating stage operations.

In the following discussion of the particular terms applicable to the practice of the adsorptive separation zone of the process of our invention, it is important to realize that, unless otherwise specified, each term will have applicability to each of the two stages of the preferred adsorptive separation zone of the instant process.

As used herein, the term "feed stream" of an adsorptive stage in question is intended to indicate a stream in the process which comprises the feed material to such stage and which is charged to the bed of adsorbent associated with such stage for the purpose of recovering or rejecting the desired component(s) of the feed material. The feed stream to such stage will comprise one or more extract components and one or more raffinate components. An "extract component" is a chemical compound which is preferentially adsorbed by the adsorbent associated with such stage as compared to a "raffinate component". Normally, the term "extract component" is synonymous with the desired product of the process. However, since our process comprises a two-stage rejective and adsorptive operation with respect to 2,6-DMN, this is not necessarily so. For instance, in the preferred embodiment of the adsorptive separation zone of the subject process, the second stage of the adsorptive separation zone is operated at 2,6-DMN extractive conditions, that is to say, 2,6-DMN is selectively adsorbed compared to other material present in the second stage feed material and is the extract component which is recovered as the second stage product. Note however that the 2,6-DMN is rejected during the first stage to the raffinate stream and thus, although 2,6-DMN is the desired product of the overall process of a particular stage, is not the extract component of the first stage of the process.

The extract stream of the first stage comprises mainly DMN isomers other than 2,6-DMN. The first stage extract stream is directed to a desorbent recovery zone and the recovered DMN isomer containing first stage extract product then becomes a feedstream to the isomerization reaction zone. The first stage raffinate stream comprising mainly 2,6-DMN isomers and other impurities becomes the feedstream to the second adsorptive separation stage. The second stage products differ from the first stage products in that the second stage raffinate product stream comprises various small amounts of DMN isomers including a small amount of 2,6-DMN while the second stage extract stream comprises mainly 2,6-DMN. The 2,6-DMN-rich extract of the second stage of the adsorptive separation zone would, after purification, be considered the final product of our overall process.

The term "extract stream" refers to a stream which contains extract components originally contained in the feed stream to the stage in question and which, after becoming attached to the adsorbent, have been desorbed from the bed of adsorbent by the desorbent stream. The composition of the extract stream as it leaves the bed of adsorbent will normally vary with time and can range from about 100 mole percent extract components to about 100 mole percent desorbent components. The term "raffinate stream" is intended to indicate a stream originating at the bed of adsorbent associated with the stage in question and which contains the majority of the raffinate components of the feed stream to the stage in question. The raffinate stream is basically the unadsorbed (i.e., rejected) components of the feed stream plus desorbent components which are picked up during passage through the adsorption zone. Both the extract stream and the raffinate stream are normally passed into a back-mixed accumulation zone before being passed into the respective fractionation columns for recovery of the desorbent material and purification of the extract or raffinate material associated therewith.

As used herein, the term "desorbent" is intended to indicate a chemical compound capable of desorbing the extract component from the bed of adsorbent. A "desorbent stream" is a process stream in which the desorbent is carried to the bed of adsorbent. The desorbent is preferably a hydrocarbon which may be separated from the extract and the raffinate components quite readily by fractional distillation. The desorbent should therefore have a different boiling point, preferably lower than both the extract and raffinate components. In the preferred embodiment of our invention, the desorbent stream most useful in this invention should contain an aromatic compound and is preferably rich in toluene or chlorobenzene and most preferably is chlorobenzene.

Configurations for the adsorptive separation zone and the preferred simulated moving bed technique is described in some detail in U.S. Pat. Nos. 3,392,113; 3,455,815; 4,006,197; and 2,985,589 which are incorporated herein by reference. The references describe operating conditions and methods and adsorbents for use in the separation of hydrocarbons. Further information on adsorptive techniques and the preferred operating methods may be obtained by reference to U.S. Pat. Nos. 3,617,504; 4,133,842; and 4,434,051 which are incorporated herein by reference. Information on a suitable rotary valve design is available in U.S. Pat. No. 3,040,777.

Another embodiment of a simulated moving bed flow system suitable for use in the process of the present invention is the cocurrent high efficiency simulated moving bed process disclosed in U.S. Pat. No. 4,402,832 incorporated herein by reference in its entirety.

The preferred operating conditions for the adsorbent containing chambers used in the separation stage include a temperature of from 20° to about 250° C. and a pressure of from atmospheric to about 1500 kPag. The pressure is normally set as being sufficient to maintain liquid phase conditions within all points of the adsorptive separation process. A temperature of from 150° to 200° C. and a pressure between 800 and 1200 kPag are highly preferred. The adsorbents which are most preferred for the separation of 2,6-DMN from a feed mixture comprising 2,6-DMN and its isomers comprise a potassium exchanged, X-type zeolite adsorbent and a carbon adsorbent having a pore opening of a size sufficient to allow the 2,6-DMN and desorbent molecules access thereto without undue interference therewith. Activated carbons are the most preferred carbon adsorbent with such activated carbon being exemplified by the type commerically available as "Type OL-Carbon" from the Calgon Corporation.

As mentioned above, the adsorptive separation zone produces two by-product streams that are not useful as product streams of this invention. These two streams are the first adsorptive stage extract stream and the second adsorptive stage raffinate streams. Both of these streams comprise mixtures of DMN isomers including small amounts of 2,6-DMN. Typically, the first adsorptive stage extract stream will have the greater volume of the two by-product streams. To maximize the efficiency of the instant continuous process, both of these by-product streams may be processed further in the isomerization reaction zone.

The second adsorptive stage raffinate stream comprising various DMN isomers including 2,6-DMN may be directed as a portion of the feedstock to the isomerization reaction zone. Using a platinum group metal containing isomerization catalyst promotes the formation of indanes and tetralins from the 1,7 and 2,7 isomers of DMN which are difficult to isomerize into 2,6-DMN. Recycling the raffinate stream to the isomerization step promotes the conversion of indanes and tetralins into 1,6 and 2,6-DMN isomers, thus converting the 1,7 and 2,7-DMN isomers indirectly into the desired 2,6-DMN isomer. Therefore, the recycling of the second adsorptive stage raffinate stream to the isomerization reaction step improves the overall efficiency of this continuous process. The first adsorbent stage extract by-product stream on the other hand typically comprises large amounts of DMN isomers which make this stream an excellent feedstock for the isomerization reaction step of the instant continuous process where it may be converted into a product comprising greater amounts of 2,6-DMN isomers.

The isomerization reaction step of the instant process comprises an isomerization reaction zone containing an isomerization catalyst and operating at isomerization reaction conditions such that the product stream of the isomerization reaction zone contains a greater amount of 2,6-DMN than the feedstream to the isomerization reaction zone. The isomerization reaction can be conducted over a wide range of temperatures, but, in general, in the range from about 100° C. to about 500° C. is preferred. Space velocities from about 0.1 to about 10 liquid volumes per hour of isomerizable hydrocarbons per volume of catalytic composite are preferred with reaction zone pressures preferably within the range from about 1 to about 70 atmospheres. The isomerization reaction may be accomplished in the presence of hydrogen preferably in the range from about 0.5 to about 10 moles of $H_2$ per mole of isomerizable hydrocarbon. The function of the hydrogen is primarily to improve catalyst life, apparently by preventing polymerization of intermediate reaction products which would otherwise polymerize and deposit on the catalytic composite. However, it is anticipated that the isomerization reaction may occur in the presence of very little hydrogen, "very little" hydrogen being equal to or less than the equilibrium solubility level of hydrogen in the hydrocarbons being isomerized. The use of only soluble hydrogen in this isomerization reaction would enable the process to be operated without gas separation or conveying equipment normally associated with a process using excess hydrogen as a feed component. If excess hydrogen is used, it is not necessary to employ pure hydrogen since hydrogen containing gases, e.g., hydrogen-rich gas from the catalytic reforming of naphthas are suitable.

Preferably, a hydrocarbon feedstock to the isomerization reaction zone containing DMN isomers is isomerized at isomerization reaction zone conditions most suitable for the isomerization of DMN into 2,6-DMN, which conditions include a temperature of from 300° to 450° C., a pressure of from 1 to 20 atmospheres, a liquid hourly space velocity of from 0.5 to 5 $hr^{-1}$, and a hydrogen to hydrocarbon molar feed ratio of from 1 to 7.

As mentioned above, the anticipated feedstock to the isomerization reaction zone of the instant combination process is the first adsorbent stage extract by-product stream and possibly the second stage raffinate stream. However, any hydrocarbon stream rich in DMN isomers except the 2,6 isomer could conceivably be utilized as a portion to all of the feedstock to the isomerization reaction zone. Thus, an external feedstream containing various DMN isomers could be first directed to the isomerization step of this invention. The absence of large quantities of 2,6-DMN in the DMN isomer-containing feedstock of the isomerization reaction zone is very important. The typical isomerization catalyst is restricted by equilibrium to producing a product comprising 8.0 to 20.0 wt. % 2,6-DMN. This means that the catalyst is not efficiently utilized for converting feedstocks comprising say 5.0 wt. % 2,6-DMN in the feed as the incremental change in 2,6-DMN concentration between the feed and product is low. However, this does not mean that one is prevented from utilizing a feedstock comprising significant amounts of 2,6-DMN. It means simply that the isomerization reaction zone of the instant process is most effective in converting a feedstock comprising DMN isomers but also comprising as little 2,6-DMN isomer as possible into a product containing greater amounts of 2,6-DMN.

A further important aspect of the isomerization zone of the present continuous process is the choice of isomerization catalyst. At least two concerns must be satisfied by the choice of isomerization catalyst. The first concern is choosing a catalyst that is capable of converting non-2,6-DMN isomers into 2,6-DMN at high conversion. The reason for choosing a high conversion catalyst is obvious in that the non-2,6-DMN isomer comprising hydrocarbon feed rate to the isomerization can be reduced in proportion to the increasing conversion ability of the isomerization catalyst chosen. In this respect, it has been determined that an isomerization catalyst comprising a crystalline aluminosilicate zeolite bound with a refractory oxide support exhibits a desirable DMN isomer conversion activity. Preferably, the catalyst will comprise from 5.0 to 60.0 wt. % of a crystalline aluminosilicate zeolite, as this proportion of zeolite in the catalyst had been determined to be most effective in the isomerization of DMN isomers into the 2,6 isomer.

A second major desirable characteristic of the isomerization catalyst of this invention is the ability of the catalyst to convert difficult-to-process isomers of DMN especially the 1,7 and 2,7 isomers of DMN into 2,6-DMN. If the isomerization catalyst is unable to isomerize the difficult isomers into 2,6-DMN, then these undesirable isomers of DMN would necessarily accumulate in the continuous process unless a drag stream removing the accumulated undesirable isomers was employed in the process. The minimization or elimination of such a drag stream is an important aspect in selecting the isomerization catalyst.

It has been found that the addition of a platinum group metal component to the crystalline aluminosilicate zeolite/refractory oxide isomerization catalyst above succeeds in essentially eliminating the accumulation of non-2,6-DMN isomers from the continuous process of this invention. It appears that the platinum group metal component succeeds in hydrogenating a portion of difficult-to-isomerize DMN isomers into dimethyltetralins which are readily isomerized by the isomerization catalyst and are subsequently dehydrogenated to 2,6-DMN or other easy-to-isomerize DMN isomers.

The catalyst composition most useful in the present isomerization reaction zone comprises from 0.1 to 5.0 wt. % of a platinum group metal component, from 5.0 to 60.0 wt. % of a crystalline aluminosilicate zeolite, and from about 35.0 to 94.9 wt. % alumina. We have found that significant improvements in isomerization performance are realized when the crystalline aluminosilicate content of the catalyst composition is less than 60.0 wt. %. In addition, we have found that the incorporation of a platinum group metal component results in an isomerization reaction product in which the 2,6 isomer of DMN is present in an amount higher than that of the feedstock.

The metal that is present in the catalyst composition to supply the hydrogenation-dehydrogenation function is a platinum group metal. The platinum group metals include the metals platinum, iridium, osmium, palladium, rhodium, and ruthenium. The preferred platinum group metal is platinum. As mentioned, the platinum group metal component of the catalytic composition of the present invention will be utilized in an amount from about 0.1 to about 5.0% by weight of the composition. It is particularly preferred that the metal component concentration in the isomerization catalyst be at least about 0.1% by weight and not more than about 2% by weight.

Of course, it is not beyond the scope of the instant invention that the catalyst composition contain a catalytically effective amount of a promoter metal. Examples of such promoter metals include tin, lead, germanium, cobalt, nickel, iron, tungsten, chromium, molybdenum, bismuth, indium, gallium, cadmium, zinc, uranium, copper, silver, gold, tantalum, one or more of the rare earth metals, and mixtures thereof.

Another essential component of the instant invention is the crystalline aluminosilicate zeolite. The crystalline aluminosilicate zeolite useful as a portion of the isomerization catalyst of the instant process may be selected from any known crystalline aluminosilicate zeolites known in the prior art. Crystalline aluminosilicates contemplated as being particularly useful in the isomerization catalyst of this invention include mordenite, Y-type zeolites, L-type zeolites, omega zeolites, and the ZSM series of zeolites including ZSM-5. Mordenite is the preferred crystalline aluminosilicate zeolite of the isomerization catalyst. While mordenite is naturally occurring, a variety of synthetic mordenites are available commercially, usually in a powder form. These synthetic mordenites can be obtained in both the sodium form and hydrogen form and at varied silica-to-alumina ratios. It is a preferred embodiment of the present invention that the mordenite be of the hydrogen form and that the silica-to-alumina ratio of the mordenite be at least 16:1, and more preferably in the range from 16:1 to 60:1.

The hydrogen form mordenite is incorporated with a refractory oxide binder, preferably alumina, and formed into a catalytic composite. The formed catalytic composite may be prepared by any known method in the art including the well-known oil drop and extrusion methods. The hydrogen form mordenite may be present in an amount within the range of 5.0 to about 60.0 wt. %, preferably within the commercially desirable range of 20.0 to about 50.0 wt. %. Thus, the alumina is preferably present in an amount within the range of from about 40.0 to about 95.0 wt. %, based on total weight of the unpromoted catalyst composition.

The preferred alumina for use in the present invention is selected from the group consisting of gamma-alumina, eta-alumina, and mixtures thereof. Most preferred is gamma-alumina. Other refractory inorganic oxides which are contemplated include, for example, silica gel, silica-alumina, magnesia-alumina, zirconia-alumina, phosphorus-containing alumina, and the like.

The platinum group metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the refractory oxide support with a solution or suspension of a decomposable compound of a platinum group metal. For example, platinum may be added to the support by commingling the latter with an aqueous solution of chloroplatinic acid. Another acid, for example nitric acid or other optional component, may be added to the impregnating solution to further assist in dispersing or fixing the platinum group metal component in the final catalyst composite. The platinum group metal component may be located upon the catalyst in a variety of useful manners known in the art including uniformly dispersed, surface-impregnated, or surface-concentrated among others.

The isomerization catalyst prepared as described above and utilized in the isomerization reaction zone produces an isomerization reaction zone product comprising isomers of DMN including a substantial amount of 2,6-DMN as well as hydrocarbons that are lighter and heavier in molecular weight than the DMN isomers. This isomerization reaction zone product stream is directed as a recycle stream to the fractionation zone described above and the process repeats.

EXAMPLE I

Three isomerization catalysts, one of the instant invention and two not of this invention, were prepared as set forth below. A mixture of powders of hydrogen form, low sodium synthetic mordenite (marketed by Union Carbide under the name LZ-M8) and alumina was prepared. The powder precursor for Catalyst A of this invention and Catalyst B, not of this invention, comprised a 1:1 weight ratio mixture of mordenite and alumina. The powder precursor for Catalyst C, not of this invention, comprised a 9:1 weight ratio of mordenite to alumina. The powder precursor for each catalyst was mixed with an acidified peptization solution and extruded by means well known in the art. The extruded composite was then dried and calcined.

Catalysts A and C were then impregnated with platinum. Both extrudates A and C were contacted with an acidified solution of chloroplatinic acid such that Catalyst A comprised 0.4 wt. % platinum and Catalyst C comprised 0.3 wt. % platinum. Catalyst B contains no catalytic modifier components. The final catalyst formulations can be found in Table 1 below.

TABLE 1

| Catalyst | Mordenite, wt. % | Alumina, wt. % | Platinum, wt. % |
|---|---|---|---|
| A | 49.8 | 49.8 | 0.4 |
| B | 50.0 | 50.0 | — |
| C | 87.8 | 9.9 | 0.3 |

EXAMPLE II

Catalyst A, of this invention, and Catalyst C, not of this invention, were evaluated for their ability to convert a DMN isomer-containing feedstock into 2,6-DMN. The propensity of each catalyst to detrimentally convert naphthalenes into non-naphthalene products was also evaluated.

The catalyst evaluation was accomplished in a laboratory-scale reactor using 10 cc of 1/16 inch extrudated of each catalyst. The pilot plant conditions included a temperature of 375° C., a pressure of 3.4 atmospheres gauge, a liquid hourly space velocity of 2 $hr^{-1}$ and a hydrogen-to-hydrocarbon molar feed ratio of 5:1. The composition of the feedstock used in the pilot plant test can be found in Table 2 below.

TABLE 2

| Feed Analysis | |
|---|---|
| Compound | Wt. % |
| Non-Aromatics | 0.00 |
| Toluene | 0.01 |
| Biphenyl | 1.04 |
| DiHydroNaphthalene | 0.43 |
| Naphthalene | 0.02 |
| 1-MeNaphthalene | 0.11 |
| 2-MeNaphthalene | 0.09 |
| 1-EtNaphthalene | 4.19 |
| 2-EtNaphthalene | 13.26 |
| 1,2 + 1,8-DiMeNaphthalene | 1.66 |
| 1,3 + 1,6-DiMeNaphthalene | 36.58 |
| 1,4-DiMeNaphthalene | 2.84 |
| 1,5-DiMeNaphthalene | 2.22 |
| 1,6-DiMeNaphthalene | 0.00 |
| 1,7-DiMeNaphthalene | 14.91 |
| 1,8-DiMeNaphthalene | 0.00 |
| 2,3-DiMeNaphthalene | 4.81 |
| 2,6-DiMeNaphthalene | 1.97 |
| 2,7-DiMeNaphthalene | 15.00 |
| Heavies | 0.86 |
| Total | 100.00 |

The results of the pilot plant testing can be found in Table 3 below.

TABLE 3

| | 2,6-DMN Product (wt. %) Catalyst | | Total $C_{12}$ Ring Loss (wt. %) Catalyst | |
|---|---|---|---|---|
| Hours On-Stream | A | C | A | C |
| 2 | 10.2 | 9.8 | 3.8 | 8.3 |
| 3 | 10.3 | 9.8 | 3.0 | 6.9 |
| 4 | 10.2 | 9.9 | 2.8 | 6.0 |
| 5 | 10.2 | 10.0 | 2.5 | 5.0 |

The results of the testing indicates that Catalyst A, the isomerization catalyst of this invention, has a slight advantage over Catalyst C in the production of 2,6-DMN from a DMN isomer-containing feedstock. However, the results also indicate that Catalyst A is much less reactive in converting DMN isomers into by-products containing greater or fewer carbon atoms than the DMN isomers. This means a continuous process using isomerization Catalyst A would retain a greater amount of non-2,6-DMN isomers in the reaction product which could be later recycled again to the isomerization reaction zone for further processing, making Catalyst A of this invention the more desirable of the two catalysts.

EXAMPLE III

Catalysts A and B were evaluated for their DMN isomerization properties in an isomerization pilot plant. The pilot plant tested 150 cc of 1/16 inch extrudates of each catalyst. The testing conditions included a temperature of 375° C., a pressure of 3.4 atmospheres guage, a liquid hourly space velocity of 2.0 $hr^{-1}$, and a hydrogen-to-hydrocarbon molar ratio of 5:1.

The DMN-containing hydrocarbon feed utilized in the isomerization reaction zone is characterized in Table 2. The catalysts were compared for their stability over time for producing 2,6-DMN, for converting 1,3- and 1,6-DMN isomers into other products and for converting difficult-to-convert 1,7- and 2,7-DMN isomers into other DMN and non-DMN products. The comparison can be found in Table 4 below.

TABLE 4

| Hours On-Stream | 2,6-DMN Product (wt. %) Catalyst A | 2,6-DMN Product (wt. %) Catalyst B | 1,3- + 1,6-DMN Conversion (%) Catalyst A | 1,3- + 1,6-DMN Conversion (%) Catalyst B | 1,7- + 2,7-DMN Conversion (%) Catalyst A | 1,7- + 2,7-DMN Conversion (%) Catalyst B |
|---|---|---|---|---|---|---|
| 20 | 10.1 | 8.9 | 30.5 | 25.0 | 10.2 | 1.8 |
| 40 | 10.0 | 8.1 | 30.0 | 21.0 | 8.0 | 1.1 |
| 60 | 9.8 | 7.9 | 30.0 | 19.5 | 7.2 | 3.0 |
| 80 | 9.8 | 7.1 | 30.0 | 17.5 | 6.6 | 1.0 |
| 100 | 9.75 | 6.9 | 29.5 | 16.5 | 5.8 | 1.2 |
| 120 | 9.75 | 7.0 | 29.5 | 15.5 | 6.4 | 2.7 |
| 140 | 9.65 | 6.8 | 29.5 | 15.0 | 6.4 | 2.4 |
| 160 | 9.6 | — | 29.5 | — | 6.0 | — |

It is obvious from the pilot plant results that Catalyst A (a 50 wt. % mordenite, 0.4 wt. % platinum-containing catalyst) is superior in DMN isomerization ability in comparison to Catalyst B of the same formulation except absent platinum. The ability of Catalyst A to produce 2,6-DMN and to convert the various DMN isomers into other hydrocarbon products is obvious from the data in Table 4, and therefore, Catalyst A of this invention is the superior DMN isomerization catalyst of the two tested.

EXAMPLE IV

A simulated countercurrent moving bed plant of the type described above and corresponding to the schematic flowsheet described in the Drawing was prepared for operation at the following conditions:

| | |
|---|---|
| Adsorbent Type | Potassium-exchanged X zeolite |
| Adsorbent Volume | 515 cc |
| Feed Rate | 28.0 cc/hr |
| Desorbent Rate | 500 cc/hr |
| Rotary valve cycle time | 1.0 hour |
| Operating Temperature | 200° C. |
| Desorbent | 100% Toluene |
| Feed Composition | |

| Component | Wt. % |
|---|---|
| 2,6-DMN | 12.5 |
| Other DMN | 57.3 |
| Others | 30.2 |
| Total | 100.0 |

The plant was operated at the above conditions in the 2,6-DMN rejective mode, that is, in such manner so that the 2,6-DMN preferentially is directed to the raffinate stream. In so doing, during one particular test run of the plant, 85 cc/hr of raffinate product was obtained:

First Stage Raffinate Product Composition (On a Desorbent-Free Basis

| Component | Wt. % |
|---|---|
| 2,6-DMN | 68.2 |
| Other DMN | 2.8 |
| Others | 29.0 |
| Total | 100.0 |

This first stage raffinate stream was then directed to storage in preparation for Stage 2 of our process.

For Stage 2, the same simulated moving bed plant which was used for Stage 1 was prepared for operation at the following conditions:

| | |
|---|---|
| Adsorbent Type | same as Stage 1 |
| Adsorbent Volume | same as Stage 1 |
| Feed Rate | 27.5 cc/hr |
| Desorbent Rate | 550 cc/hr |
| Rotary valve step time | 1.0 hour |
| Operating Temperature | 175° C. |
| Desorbent | 100% Toluene |

During the second stage of our process, the plant was operated at the above conditions in the extractive mode, that is, in such manner so that the 2,6-DMN preferentially is directed to the extract stream. The feed to the pilot plant during this second stage of our process was a desorbent-free portion of the composite of the first stage raffinate product obtained over a period of time and numerous test runs.

Second Stage Feed Composition (On a Desorbent-Free Basis)

| Component | Wt.% |
|---|---|
| 2,6-DMN | 71.5 |
| Other DMN | 1.2 |
| Others | 27.3 |
| Total | 100.0 |

In so doing, 265 cc/hr of extract product was obtained:

Second Stage Extract Product Composition (on a Desorbent-Free Basis)

| Component | Wt. % |
|---|---|
| 2,6-DMN | 78.2 |
| Other DMN | 1.5 |
| Others | 20.3 |
| Total | 100.0 |

Because this second stage extract product purity (that is, wt. % 2,6-DMN) obtained was lower than the commercially desirable value of 90.0 wt. %, a further distillative fractionation was performed to remove otherwise easily fractionatable impurities. The resultant product of this final finishing distillation was over 90.0 wt. % 2,6-DMN. The ultimate loss of 2,6-DMN during such distillation would be dependent upon the sophistication of the fractionation means employed. It should be mentioned that such final finishing distillation procedure may or may not be necessary, depending upon the extent to which impurities are present in the feed to the first stage of our process. Obviously, insofar as no change in properties of these impurities occurs in the course of our two-stage process, such material may be fractionated prior to processing in our process, rather than subsequent thereto, in accordance with the requirements of the specific commercial installation.

EXAMPLE V

A simulated countercurrent moving bed pilot plant of the type described above was prepared for operation at the conditions specified in Example IV for the first stage operation, thereby producing a first stage raffinate product stream equivalent to that obtained in Example IV. This product stream was then directed to storage in preparation for Stage 2 of our process.

For stage 2, a simulated moving bed pilot plant of the same type which was used for Stage 1 was prepared for operation at the following conditions:

| | |
|---|---|
| Adsorbent Type | Calgon Type OL Carbon |

| Adsorbent Volume | 515 cc |
|---|---|
| Feed Rate | 32.4 cc/hr |
| Desorbent Rate | 666 cc/hr |
| Rotary valve cycle time | 1.0 hour |
| Operating Temperature | 200° C. |
| Desorbent | 100% Toluene |

In so doing, 334 cc/hr of extract product was obtained:

| Second Stage Extract Product Composition (On a Desorbent-Free Basis) | |
|---|---|
| Component | Wt. % |
| 2,6-DMN | 94.2 |
| Other DMN | 1.3 |
| Others | 4.5 |
| Total | 100.0 |

Thus, the purity of the ultimate 2,6-DMN product produced by this embodiment of our invention was commercially acceptable (i.e., ò 90.0 wt. % 2,6-DMN) without the need to perform a finishing distillation step.

EXAMPLE VI

A simulated countercurrent moving bed pilot plant of the type described above was prepared for operation at the following conditions:

| Adsorbent Volume | 515 cc | |
|---|---|---|
| Feed Rate | 28.0 cc/hr | |
| Desorbent Rate | 520 cc/hr | |
| Rotary valve cycle time | 1.0 hour | |
| Operating Temperature | 170° C. | |
| Desorbent | 100% Monochlorobenzene | |
| Feed Composition | Component | Wt. % |
| | 2,6-DMN | 10.5 |
| | Other DMN | 52.2 |
| | Others | 37.3 |
| | Total | 100.0 |

The plant was operated at the above conditions in the 2,6-DMN rejective mode, that is, in such manner so that the 2,6-DMN was preferentially directed to the raffinate stream. In so doing, 160 cc/hr of raffinate product was obtained:

| First Stage Raffinate Product Composition (On a Desorbent-Free Basis) | |
|---|---|
| Component | Wt. % |
| 2,6-DMN | 60.9 |
| Other DMN | 1.1 |
| Others | 38.0 |
| Total | 100.0 |

This first stage raffinate product stream was then directed to storage in preparation for Stage 2 of our process.

For Stage 2, a simulated moving bed pilot plant of the same type used for Stage 1 was prepared for operation at the following conditions:

| Adsorbent Type | Calgon Type OL Carbon |
|---|---|
| Adsorbent Volume | 515 cc |
| Feed Rate | 10.6 cc/hr |
| Desorbent Rate | 525 cc/hr |
| Operating Temperature | 170° C. |
| Desorbent | 100% Monochlorobenzene |

The feed to the pilot plant during this second stage of our process was, as aforesaid, a desorbent-free portion of the first stage raffinate product. Hence, the composition of the feed stream to Stage 2 of our process in this example was as follows:

| Second Stage Product Composition (On a Desorbent-Free Basis) | |
|---|---|
| Component | Wt. % |
| 2,6-DMN | 75.4 |
| Other DMN | 1.1 |
| Others | 25.5 |
| Total | 100.0 |

The plant was operated at the above conditions in the 2,6-DMN extractive mode, that is, in such a manner so that the 2,6-DMN is preferentially directed to the extract stream. In so doing, 160 cc/hr of extract product was obtained:

| Second Stage Extract Product Composition (On a Desorbent-Free Basis) | |
|---|---|
| Component | Wt. % |
| 2,6-DMN | 95.8 |
| Other DMN | 1.3 |
| Others | 2.9 |
| Total | 100.0 |

DISCUSSION OF EXAMPLES IV, V, AND VI

In general, the above data does show that a two-stage adsorptive separation zone provides a 2,6-DMN selective system with adequate selectivities for the commercial use thereof. It has been shown, specifically, that one embodiment of the present invention is capable of upgrading the 2,6-DMN purity of a feed mixture from approximately 12.5 wt. % to over 78.0 wt. %, which product, in turn, was shown to be easily fractionatable by common distillation to obtain a commercially acceptable final product purity of over 90.0 wt. %, although such adsorption/distillation process is not the preferred embodiment of our invention.

The foregoing Examples V and VI also demonstrate the superiority, with respect to ultimate product purity, of the preferred embodiments of the adsorptive separation zone of the continuous process of our invention compared to that demonstrated by Example IV. In Example V, the 2,6-DMN product purity was in excess of 94.0 wt. % and in Example VI, the 2,6-DMN product purity exceeded 95.0 wt. %. Thus, in both Examples V and VI, it has been demonstrated that a commercially acceptable 2,6-DMN product may be obtained without the requirement of the final distillation, crystallization, or other non-adsorptive separation techniques of the prior art.

What is claimed is:

1. A continuous process for the production of 2,6-dimethylnaphthalene including a two-stage adsorptive separation zone for obtaining purified 2,6-dimethylnaphthalene which comprises the steps of:
   (a) separating in a fractionation zone a feed stream comprising dimethylnaphthalene isomers and hydrocarbons with boiling points greater than and less than the dimethylnaphthalene isomers to produce a first process stream comprising essentially dimethylnaphthalene isomers;

(b) passing the first process stream comprising essentially dimethylnaphthalene isomers into an adsorptive separation zone comprising a first stage, employing a first stage adsorbent comprising a potassium-exchanged X-zeolite and a first stage desorbent material and operating at 2,6-dimethylnaphthalene rejective conditions and isomer adsorbtive conditions to adsorb said isomer from said feed mixture to yield a first stage raffinate product containing 2,6-dimethylnaphthalene with at least a portion of the first stage raffinate product being fed to a second stage, employing a second stage adsorbent comprising a potassium-exchanged X-zeolite and a second stage desorbent material and operating at 2,6-dimethylnaphthalene adsorptive conditions, to adsorb 2,6-dimethylnaphthalene thereby producing a second stage raffinate product and a second stage extract product containing purified 2,6-dimethylnaphthalene (c) recovering the second stage extract product containing purified 2,6-dimethylnaphthalene;

(d) admixing the first stage extract product with the second stage raffinate product produced in zone (b) to produce an isomerization reaction step feedstock and contacting the isomerization reaction zone feedstock with an isomerization catalyst comprising a crystalline aluminosilicate zeolite and a platinum group metal component at isomerization reaction conditions in an isomerization reaction zone to produce an isomerization reaction zone product stream, characterized in that the concentration of the 2,6-dimethylnaphthalene isomer in the isomerization reaction zone product stream is greater than the concentration of the 2,6-dimethylnaphthalene isomer in the isomerization reaction step feedstock; and (e) passing the isomerization reaction zone product stream into the fractionation zone (a).

2. The process of claim 1 further characterized in that a fresh feed stream comprising dimethylnaphthalene isomers is introduced into the fractionation zone along with the isomerization reaction zone product stream from step (e).

3. The process of claim 1 further characterized in that the isomerization reaction zone operates at isomerization reaction conditions including a temperature of from 100° to 500° C., a pressure of from 1 to 70 atmospheres, and a liquid hourly space velocity of from 0.5 to 10 $hr^{-1}$.

4. The process of claim 3 further characterized in that the isomerization reaction zone feedstock is admixed with hydrogen at a molar feed ratio of hydrogen to hydrocarbons of from 0.5 to 10 before entering the isomerization reaction step.

5. The process of claim 3 further characterized in that the isomerization reaction zone feedstock entering the isomerization reaction zone contains hydrogen in an amount that is equal to or below the solubility limit of hydrogen in the hydrocarbons of the first process stream.

6. The process of claim 3 further characterized in that the adsorptive and desorptive conditions include a temperature within the range of from about 20° C. to about 200° C. and a pressure sufficient to maintain liquid phase.

7. The process of claim 3 further characterized in that the first and second desorbent materials used in the selective adsorption zone of step (b) is an aromatic hydrocarbon.

8. A continuous process for the production of 2,6-dimethylnaphthalenes including a two-stage adsorptive separation zone which comprises the steps of:

(a) passing a feed mixture of a feed stream comprising a mixture of dimethylnaphthalene isomers including 2,6, 2,7, and 1,7 isomers and the isomerization reaction zone product stream of step (e) below, into a fractionation means;

(b) separating the feed mixture in the fractionation means into hydrocarbon fraction having a boiling point higher than DMN isomers, a hydrocarbon fraction having a boiling point higher than DMN isomers, and into a first process stream fraction comprising dimethylnaphthalene isomers including 2,6, 1,7, and 2,7 isomers of dimethylnaphthalene;

(c) passing the first process stream into a two-stage adsorptive separation zone comprising a first stage employing a first stage adsorbent comprising a potassium-exchanged X-zeolite and a first stage desorbent material and operating at 2,6-dimethylnaphthalene rejective conditions to produce a first stage extract and raffinate product, with at least a portion of the raffinate product of the first stage being fed to a second stage, employing a second stage adsorbent comprising a carbon material and a second stage desorbent material and operating at 2,6-dimethylnaphthalene adsorptive conditions, thereby producing a second stage extract product containing purified 2,6-dimethylnaphthalene and a second stage raffinate stream;

(d) recovering the second stage extract stream containing purified 2,6-dimethylnaphthalene;

(e) feeding the first stage extract stream and the second stage raffinate stream into an isomerization reaction zone operating at isomerization reaction conditions including a temperature of from 300° to 450° C., a pressure of from 1 to 20 atmospheres, and a liquid hourly space velocity of from 0.5 to 5 $hr^{-1}$ and into contact with an isomerization catalyst comprising from 10.0 to 60.0 wt. % of a crystalline aluminosilicate and from 0.1 to 5.0 wt. % of a platinum group metal component to produce an isomerization reaction zone product stream having a 2,6-dimethylnaphthalene concentration greater than that of the feed entering the isomerization reaction step; and (f) passing the isomerization reaction zone product into the fractionation means of step (a).

9. The process of claim 8 further characterized in that the crystalline aluminosilicate zeolite component of the isomerization catalyst is mordenite.

10. The process of claim 8 further characterized in that the aromatic desorbent useful as the desorbent of the first and second adsorbent stages is either toluene or chlorobenzene.

11. The process of claim 10 further characterized in that the carbon adsorbent material of the second stage of the adsorptive separation zone is a carbon material having a pore opening sufficiently large to permit the adsorption and desorption of 2,6-dimethylnaphthalene and the desorbent material.

12. The process of claim 8 further characterized in that each adsorptive zone is effected with a static bed system.

13. The process of claim 8 further characterized in that each adsorptive zone is effected with a simulated moving bed flow system.

14. The process of claim 13 further characterized in that the simulated moving bed is operated in either a cocurrent or countercurrent manner.

15. The process of claim 8 further characterized in that the Group VIII metal component of the isomerization catalyst is platinum.

16. The process of claim 15 further characterized in that the platinum component of the isomerization catalyst is present in an amount ranging from 0.1 to 2.0 wt. %.

17. The process of claim 16 further characterized in that the isomerization catalyst comprises an alumina binder.

18. The process of claim 16 further characterized in that the adsorptive and desorptive conditions of the first and second adsorptive separation zone includes a temperature of from 20° to 200° C. and a pressure sufficient to maintain liquid phase.

* * * * *